United States Patent [19]
Clark, Jr. et al.

[11] Patent Number: 6,110,134
[45] Date of Patent: Aug. 29, 2000

[54] GEL PADDED THERMOPLASTIC SPLINT

[75] Inventors: John N. Clark, Jr., Cedarburg; Matthew J. Mercier, Germantown, both of Wis.

[73] Assignee: Smith & Nephew, Inc., Memphis, Tenn.

[21] Appl. No.: 08/823,258

[22] Filed: Mar. 24, 1997

[51] Int. Cl.$^7$ ........................................ A61F 5/00
[52] U.S. Cl. ........................................ 602/6; 602/8
[58] Field of Search ................................ 602/6, 8

[56] References Cited

U.S. PATENT DOCUMENTS

| | | | |
|---|---|---|---|
| 3,850,167 | 11/1974 | Seeley | 128/87 R |
| 4,193,395 | 3/1980 | Gruber | 128/90 |
| 4,240,415 | 12/1980 | Wartman | 128/90 |
| 4,516,572 | 5/1985 | Schlein | 128/156 |
| 4,842,931 | 6/1989 | Zook | 428/354 |
| 5,205,815 | 4/1993 | Saunders | 602/19 |
| 5,334,135 | 8/1994 | Grim et al. | 602/26 |
| 5,384,913 | 1/1995 | Hendry | 2/2 |
| 5,445,602 | 8/1995 | Grim et al. | 602/27 |
| 5,456,658 | 10/1995 | Duback et al. | 602/8 |
| 5,633,286 | 5/1997 | Chen | 524/474 |

OTHER PUBLICATIONS

Silon STS; Jobst Silicon Thermoplastic Splinting for Scar Management.
AliMed; Soft Splint Assortment, p. S128.
Smith & Nephew Rolyan, splinting materials, catalogue pp. 4, 5, 12, 82–85.

*Primary Examiner*—Richard J. Apley
*Assistant Examiner*—Kelvin E. Hart
*Attorney, Agent, or Firm*—Garvey, Smith, Nehrbass & Doody, LLC

[57] ABSTRACT

A low temperature synthetic splint/orthotic material having affixed thereto a layer of gel-like viscoelastic padding having a compressibility such that upon normal application of the padded splinting material to a body part exhibiting such as bony prominences, that the padding compresses but does not bottom out under normal usage whereby the bony prominence is supported over its extent along with the rest of the body part. In preferred embodiments a cover of fabric, foam or polymeric film is bonded over the viscoelastic padding to isolate body tissue from possible discomfort associated with some properties of the padding material.

36 Claims, 1 Drawing Sheet

GEL PADDED THERMOPLASTIC SPLINT

BACKGROUND OF THE INVENTION

1. Field of the Invention

This invention relates to the medical arts and particularly to splinting devices including those orthopedic supports utilized during tissue healing and rehabilitation such as the healing of bones following fracture. Additional applications of the present invention include splinting devices for immobilization and support following soft tissue disorders, rheumatological joint disease and neurological conditions that result in muscle or tissue disease requiring support. Orthopedic rehabilitation usually occurs in successive phases from the acute phase immediately following injury or surgery; the intermediate phase of continued tissue healing where immobilization stabilized the injury for continued healing and the chronic phase where prolonged rehabilitation may be necessary. Support and protection of the injured tissues are conventionally provided by one or more of splinting materials available including plaster, premolded polymers and thermoplastic "custom" formable polymers.

For many years plaster casts provided the accepted mode of fracture fixation or immobilization of joints or other body tissue during healing. Plaster has now been replaced with a variety of synthetic materials, many of which are thermoforming materials which allow a more expeditious and accurate casting or immobilization of the affected portion of the body. Synthetic casting materials are now readily available in sheet stock and pre-forms which are cut to accommodate particular body parts or joints such as arms, wrists and hands as well as torso supports, shoe inserts cervical braces, back braces, foot supports, lower extremity diabetic foot care products, wheel chair inserts, cervical braces and total contact casting applications. It is now common that these splinting materials are made of a low temperature thermoplastic material, meaning that they may be custom formed in a plastic state at a comparatively low temperature however, when in the cooled state (ambient air/body temperature) they are sufficiently rigid to provide the support and protection to healing bones and tissue. If the splinting material is in sheet stock, it is cut in known manner to the approximate shape for application to the particular area of the body to be treated. Such low temperature thermoplastic materials are typically heated to temperatures in the vicinity of 160° to 175° F. in either a heated water bath or a hot air/conventional oven, at which temperature the material is formable on the body part to be splinted. The pliable, warmed splinting material is then fitted over the body part to be supported and is molded and trimmed to the final shape as the material cools and regains its rigid characteristic.

Splinting materials frequently introduce a level of discomfort to the wearer, either through buildup of moisture and/or heat in the affected region of the body. Thermoplastic splinting materials are usually available in perforated form to provide some relief to the associated discomfort. Another frequent discomfort or irritation comes from the development of pressure points where the bony prominences bear upon the formed splint. Splinting materials manufacturers offer various padding, either as supplements to the splinting materials or offer a padded thermoplastic splinting material. These padding materials are typically of wide-ranging construction including orthopedic felt, moleskin padding, various polymer foam materials, including several with adhesive backings which may be cut and directly applied to selected locations of the splint.

2. Description of the Prior Art

Splinting materials such as plaster and thermoplastic materials, when formed into splints/orthotics, are hard, uncomfortable and irritating to bony prominences which come into contact with the splint. Traditional methods to reduce pressure points are to spot pad the splint/orthotic with foam padding or gel-like padding or to push out the splint over the bony prominences to create an air pocket or cavity adjacent the prominence. Most foam padding bottoms out and becomes ineffective. Spot padding, even with such as cellular foam padding materials only reduces the pressure over the area padded, and not the entire splint/orthotic, permitting a "hot spot" of some continued discomfort or irritation. Many foam padding materials are open celled and therefore absorb water when the splint/orthotic is routinely washed. When using open celled foam materials, the splint/orthotic needs to be air dried before being reapplied to avoid skin irritation.

Spot padding, or the prepadding of the thermoplastic material with conventional padding materials prior to heating is difficult and time consuming. Air frequently gets trapped between the splinting material and the padding causing air pockets as the material is heated leading to premature separation or movement of the padding.

Prior art prepadded materials include such as Multiform Soft Splint Material from AliMed® Inc. which combines a layer of 1/16 inch Multiform™ low temperature thermoplastic material with AliPlast™ 4E, a closed cell, self-adhesive foam padding material.

Another padded splinting material is available under the name of Silon STS®, a trademark of Bio Med Sciences, Inc. This material is a combination of layers of high temperature thermoplastic rigid sheet material and a silicone elastomer and is useful for custom molding for the treatment of scar tissue. The silicone sheet is known to reduce/control scar formation. The material, since it is a high temperature thermoplastic and would burn the skin on the prolonged contact during forming the splint directly on the affected body part, requires casting of a negative plaster mold and a positive mold form to form the splint or orthotic.

The following closed and open cell foam padding materials (available from Smith & Nephew Inc, Rehabilitative Division, the assignee of the present application) include a self-adhesive and have been used to spot pad or pre-pad low temperature thermoplastic splinting materials. Other competitive companies have similar types of padding materials. All of these conventional materials bottom-out easily and are prone to air pockets when preapplied to the low temperature thermoplastic material.

Low-Tack Polycushion® Padding Material
Polycushion® Padding
Kushionflex® Padding
Rolyan® Foam Padding
Quickstick™ Padding
Plastozate® Foam Material with Self-adhesive Back
Rolyan® Contour Foam
Moleskin Rolls
Moleskin Padding
Orthopedic Felt While there are self-adhesive paddings available for use with traditional splints or the thermoplastic type, none are sufficiently resistant to bottoming out. Smith & Nephew Rehabilitation Division offers examples of such materials including a cloth-covered Sorbothane® Padding and an open celled foam sold under the trademark PPT.

SUMMARY OF THE INVENTION

In accordance with the invention claimed herein, there is disclosed a low temperature thermoplastic material pre-lined with an integral viscoelastic, gel-like material. The low temperature thermoplastic material allows the custom molding of splints/orthotics directly on a patient, eliminating the need for positive and negative molds of the body surface being treated. The gel-like padding integrally attached to the thermoplastic splint exhibits a greater capacity to absorb and distribute shock loading, even in athletic and industrial uses and provides a significantly improved resistance to bottoming out under sudden loading. The gel-like layer preferably exhibits the characteristic of stretching isotropically with the thermoplastic material as the latter is conformed to a custom application. The provision of thermoplastic splinting materials with an integral gel-like lining facilitates the fitting of a splint/orthotic to the patient by the health care professional since the lining tends also to insulate the affected body part from the latent heat of the plastic splinting material during the splint forming process.

In preferred embodiments of the invention, the thermoplastic layer of the splint includes a polycaprolactone based polymer or an isoprene rubber based material, in sheet thickness of approximately 1/32 to about one-half inches in thickness, having integrally affixed thereon preferably of a gel-like material having viscoelastic properties similar to a polyurethane, poly vinyl chloride or a silicone ranging in thickness from about 1/32 upwards to about three inches.

Covering layers of woven and non-woven fabrics, foams and polymeric films are added in alternative embodiments of the invention to isolate the body tissue from discomfort sometimes associated with the tackiness of the surface of gel-like materials.

Further alternative embodiments of the invention include the gel lined low temperature thermoplastic splinting material being perforated with a pattern of ventilation holes.

Further objects and advantages of the invention will become apparent from the following description of the preferred and alternative embodiments of the invention.

BRIEF DESCRIPTION OF THE DRAWINGS

The present invention may be more fully understood with reference to the accompanying drawings in which.

DESCRIPTION OF THE PREFERRED EMBODIMENT

Figure 1:
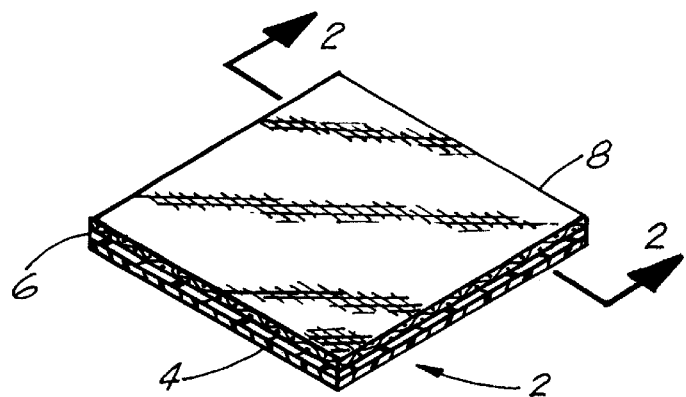
FIG. 1 is a pictorial view of one embodiment of the present invention.

A continuing problem with the forming and fitting of splints and orthotics is the molding of such a device to the irregular shapes of a body member to be fitted. Bony prominences pose particular challenges since the tissue adjacent the splint or orthotic is subject to pressure and movement against the splint which frequently results in discomfort and not uncommonly in a tissue ulceration. So common is the problem that preformed splinting materials are frequently lined with certain special padding as described above. Alternatively, such padding materials are provided separately with an adhesive backing so as to be applied in the forming process for custom fitted splints and orthotics. Unfortunately, until the present invention, a universally effective combination of formable splint/orthotic and viscoelastic padding has not been developed. It is only upon a complete recognition of the necessary compatibility of splinting and padding materials and the requirements of the padding to the formed splint that the present invention is fully understood.

Particular advantage is achieved in the present invention by fabricating the padded splinting material in a sheet material (which may be pre-cut to a preferred configuration), that it may be later formed to shape for a custom application. Preferred materials for the splint base are those synthetic casting materials providing lightweight, easily formable casts of a low temperature thermoplastic material, similar to plaster-like casts. Low temperature thermoplastic materials are those which soften under relatively low heat (e.g., below 200° F.) and are capable of being molded and shaped with hand pressure, and subsequently harden retaining the molded shape on cooling without undergoing chemical changes. A low temperature material, suitable for use as an adjustable splint should soften at sufficiently low temperatures so as to allow for molding directly on the patient without injury due to scalding or burning of the skin. Suitable polymers which melt or soften at temperatures ranging from 100° F. to 200° F. include poly (ethyleneadipate), poly (epsilon-caprolactone), polyvinyl stearate, cellulose acetate, butyrate and ethyl cellulose poly (propylene oxide) containing co-monomers, trans polyisoprene and cis polyisoprene based thermoplastic materials, and polycaprolactone based materials including commercially available polycaprolactone thermoplastic materials known as AQUAPLAST, SYNERGY, EZEFORM, POLYFORM, POLYFLEX II and SAN SPLINT, a transpoly isoprene. These thermoplastic materials are available from the Rehabilitation Division of Smith & Nephew Inc., N104, W13400 Donges Bay Road, Germantown Wis. 53022, assignee of the present invention.

A thermoplastic splinting material made according to U.S. Pat. No. 4,240,415, is incorporated herein by reference. This patent describes a thermoplastic material formed from a thermoplastic polyester having a melting point between about 100° F. and 200° F., and more particularly a poly (epsilon-caprolactone) having a weight average molecular weight of over 5,000 with a halftime crystallization at about 100° F. of between 0.5 and 10 minutes. At room temperature the poly (epsilon-caprolactone) is quite stiff with a 1% secant modulus of 50,000 psi at about 73° F. The stiffness remains high as the temperature is increased. At 140° F. some melting occurs and the stiffness modulus is 20,000 psi. Additionally, some of the poly (epsilon-caprolactone) mixtures become transparent when heated which is useful when molding and placing a splinting device on a limb such as a finger. The thermoplastic material also has 100% elastic memory which allows it to be reheated and reshaped repeatedly.

A suitable padding material for the present invention is one which may be readily bonded to the splinting material during a manufacture of the composite padded, splinting material. Bonding may be accomplished by any of several known suitable systems including adhesives such as elastomers, epoxies and solvent based adhesives or by elastomer contact adhesives, epoxies, solvent based adhesives or thermoplastic emulsions. Adhesives forming chemical or mechanical bonds are suitable for bonding. The padding materials found to be particularly effective include a viscoelastic having a gel-like property such as a polyurethane, a poly vinyl chloride or a silicone material. Such paddings for splints or supports are resilient and have the ability to return to original shape after removal from a deforming force. These resilient materials have the ability to distribute pressure around an uneven surface thereby reducing the pressure on a bony prominence by distributing the load to the surrounding area of the adjacent splint or orthotic. Since the viscoelastic material resumes its shape upon removal of the load, its resiliency continues to support the body part as it shifts within the splint or orthotic, with the load being redistributed as the body part shifts.

An additionally important aspect of the present invention is the "softness" or compressibility of the viscoelastic or silicone material. It is essential that the padding not bottom out during the normally expected loading around the bony prominences or body irregularities. Once the padding reaches the extent of its compressibility, the imposed loading on the body part sought to be protected is no longer distributed such that destructive loading on the tissue may occur. Continued exposure to tissue loading can cause abrasion, ulcers or other tissue trauma causing tissue breakdown. We have found that a convenient measure of compressibility for these padding materials is by determining the pressure per square inch load required imposed on the padding material to cause compression of no more than about 75% of its original thickness as described by the standards document ASTM D575-91. Suitable values for applications generally for splints and orthotics are those materials that will withstand pressures of from about 0.01 pound per square inch to about 20 pounds per square inch. For splinting materials for fractured or traumatized human bones and joints, a material exhibiting compression to about 75% of original thickness in response to a pressure per square inch of from about 1 to about 3 is particularly effective.

Figure 2:
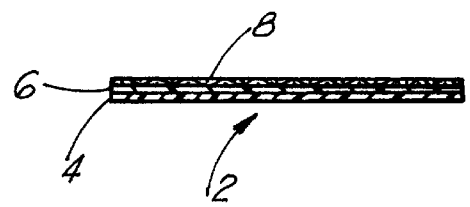
FIG. 2 is a side elevational sectional view of the embodiment of FIG. 1, taken along line 2—2.

Referring now to FIGS. 1 and 2, a sheet 2 of a composite of padded thermoplastic splinting material according to the present invention is illustrated. Sheet 2 includes the base thermoplastic material 4 as described above. Bonded to base material 4 is padding layer 6 formed of a material as described above. In a preferred form, a viscoelastic polyurethane gel-like material is extruded or cast, or otherwise laid down on material 4 as material 4 is conveyed laterally under an extrusion or coating head. In such manner, the padding layer may be chemically and/or mechanically bonded as the polyurethane or other gel-like material polymerizes or solidifies on the base material 4. The casting process preferred involves laying the thermoplastic sheet in a mold and pouring the viscoelastic material onto the sheet in liquid form.

In padded thermoplastic composites suitable for limb splints or casts, the base layer of thermoplastic material 4 is preferably from about 1/32 inches to about 3/16 inches. For these applications, padding layer is preferably from about 1/16 inches to about 3/16 inches. While these ranges are preferable, thicknesses from 1/32 to as much as three inches have been found useful. Those familiar with the art will recognize that different applications of splinting or orthotics will require varying thicknesses of thermoplastic material and padding depending upon both the degree of body irregularity to be protected and the overall load to be imposed upon the splinting or orthotic device.

Since gel-like viscoelastic materials such as polyurethane or silicone frequently have a tacky surface, it is considered within the scope of the present invention to include a comfort coating or cover 8 on the surface of the padding layer of a material pleasant to the touch. Materials such as talc, corn starch or baby powder may be dusted on the surface of padding layer 6 to form such a coating 8 (FIG. 2). Preferably, a fabric cover 8 such as a woven or non-woven cloth of a natural or synthetic (e.g., a polyester) fabric material is positioned on top of the gel-like viscoelastic padding 6 and bonded to it such that any relative movement between these two layers is minimized. Alternatively, the covering layer may be composed of a foam material, such as a closed cell polyethylene, which will form a barrier between the padding 6 and the tissue of the wearer of a splint 2. Another suitable alternative material for covering 8 is a polymeric film, similarly disposed on padding 6 such that relative movement between these two components is minimized. As with a closed cell foam, the polymeric film material will form a barrier between the gel-like padding and the tissue of the wearer of the splint such that the undesirable properties of tackiness and the like are isolated from the wearer. Such polymeric films as provide the additional benefit of a reduced friction surface such that any relative movement of the splint with respect to the tissue of the wearer is less likely to cause abrasion and tissue irritation.

Figure 3:
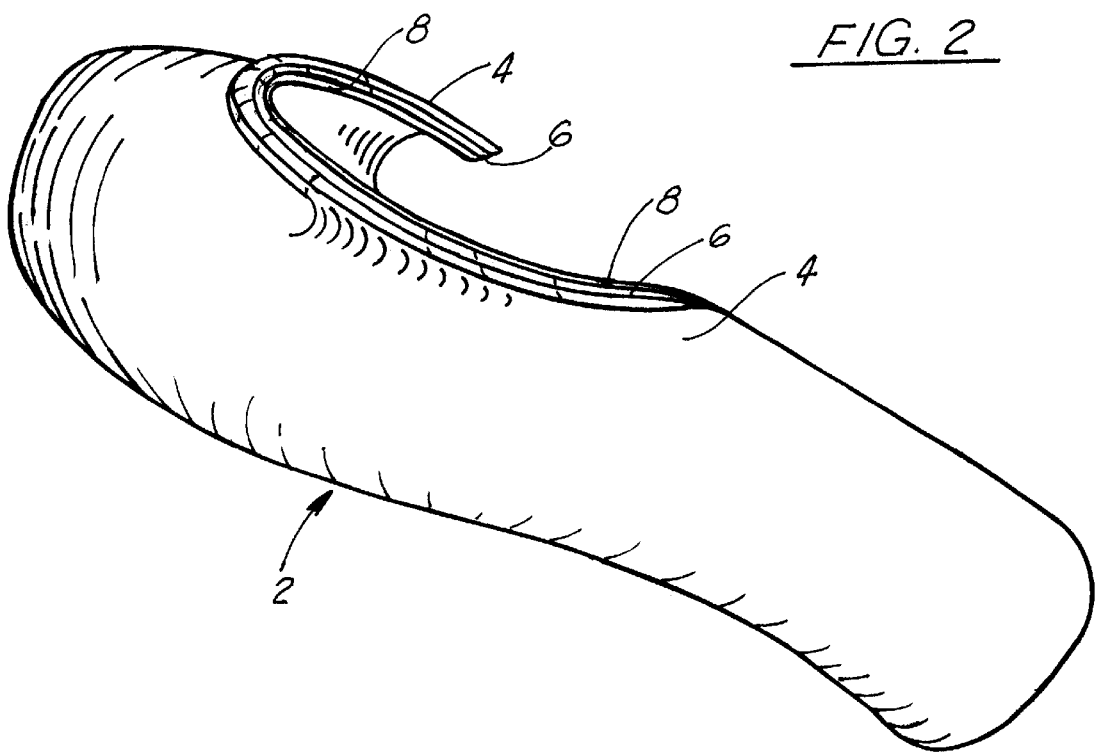
FIG. 3 is a pictorial view of a hand splint formed of the padded thermoplastic splinting material of the present invention.

FIG. 3 illustrates a sheet of splinting 2 as illustrated in FIGS. 1 and 2 which has been cut and formed to accommodate a patient's right hand. In such a splint 2, the padding layer 6 is uniformly and continuously attached to the low temperature plastic base layer 4. The particular combination of thermoplastic base 4 and padding 6 bonded over their entire adjacent surfaces permits the forming of splint 2 with a variety of curves and folds, as illustrated, such that the layers 4 and 6 stretch similarly thereby avoiding the formation of voids and discontinuities between the two layers. Even with the inclusion of cover layer 8 as described above, the integrity of the layers of splint 2 is maintained.

As alluded to earlier in the description of the action in the thermoplastic splinting material 4 and the padding 6, as the splint 2 is formed to conform to the affected body part, the splinting material 4 and the padding 6 are disposed to stretch in all directions at the "give points". In order that the multi-direction capacity of the splint to stretch, a cover 8 disposed over the padding material will also preferably exhibit the capacity to stretch in multiple directions (i.e., isotropically) with the splint 2 as it is folded or formed. The covering materials disclosed above all possess this capacity of mutual isotropic internal stretching movement when distended over or around prominences, folds or surface irregularities.

An additional alternative for the alleviation of the undesirable properties of the gel-like padding 6 is to formulate the padding to include or be later imbibed with a plasticizing oil, or therapeutic agents such as antifungals, keratolites or antiperspirants for lubrication, comfort and/or protection.

As will be apparent to persons skilled in the art, various additional modifications, adaptations and variations of the foregoing specifically disclosed embodiments and methods of coating removal may be made without departing from the objectives and scope of the present invention. Various modifications and changes may be made to the embodiments disclosed herein by those skilled in the art and such are contemplated by the present invention and are to be understood as included within the spirit and scope of the appended claims.

Accordingly, we claim:

1. A splint for being directly formed on a body part comprising
   a. A sheet of thermoplastic splinting material, which thermoplastic softens or melts in the temperature range of 100° F. TO 200° F.;
   b. A layer of gelatinous viscoelastic padding material affixed to said sheet of splinting material;
   c. said layer of padding material having a thickness and compressibility such that at least one per square inch compression force in the range of from one one-hundredth to about 20 pounds per square inch will reduce said thickness of said padding material, said reduction in thickness of said padding material being no more than about 75% of said padding material's unloaded thickness over the area of compression.

2. A splint according to claim 1 wherein said layer of padding material has a thickness and compressibility such that said at least one per square inch compression force will reduce said thickness of said padding material about 75% of its unloaded thickness over the area of compression.

3. A splint according to claim 1 wherein said layer of padding material is a gelatinous viscoelastic material comprising predominantly a polyurethane.

4. A splint according to claim 1 wherein said layer of padding material is a gelatinous viscoelastic material comprising predominantly a polyvinylchloride.

5. A splint for being directly formed on a body part comprising
   a. A sheet of low temperature thermoplastic splinting material;
   b. A layer of gelatinous viscoelastic padding material affixed to said sheet of splinting material;
   c. said layer of padding material having a thickness and compressibility such that a per square inch compression force of one one-hundredth pound per square inch will reduce said thickness of said padding material no more than about 75% of its unloaded thickness over the area of compression,
   wherein said layer of padding is a gelatinous viscoelastic material comprising predominantly a silicone.

6. A splint according to claim 5 wherein said layer of padding material has a thickness and compressibility such that a per square inch unit compression force of up to about twenty pounds will reduce said thickness of said padding material no more than about 75% of its unloaded thickness over the area of compression.

7. A splint according to claim 1 wherein said at least one per square inch compression force is in the range of between about one to about three pounds per square inch.

8. A splint according to claim 7 wherein said layer of padding material is a gelatinous viscoelastic material composed of predominantly a polyurethane.

9. A splint according to claim 7 wherein said layer of padding material is a gelatinous viscoelastic material composed of predominantly a silicone.

10. A splint for being directly formed on a body part comprising
    a. A sheet of low temperature thermoplastic splinting material;
    b. A layer of gelatinous viscoelastic padding material affixed to said sheet of splinting material;
    c. Said layer of padding material having a thickness and compressibility such that a per square inch compression force of one one-hundredth pound per square inch will reduce said thickness of said padding material no more than about 75% of its unloaded thickness over the area of compression;
    wherein said layer of padding material is affixed to said splinting material by an intermediate layer selected from the group consisting of a urethane adhesive coating, a silicone adhesive coating, and an epoxy adhesive coating.

11. A splint according to claim 10 wherein said layer of padding material is affixed to said splinting material by said intermediately layer of urethane adhesive coating.

12. A splint according to claim 10 wherein said layer of padding material is affixed to said splinting material by said intermediately layer of silicone adhesive coating.

13. A splint according to claim 10 wherein said layer of padding material is affixed to said splinting material by said intermediately layer of epoxy adhesive coating.

14. A splint according to claim 1 wherein said layer of padding material is affixed to said splinting material by an intermediate polymeric bond formed between said layers.

15. A splint according to claim 1 wherein said layer of padding material is affixed to said splinting material by an intermediate chemical bond formed between said layers.

16. A splint according to claim 1 wherein said splinting material has a surface capable of forming a mechanical bond with said layer of gelatinous material.

17. A splint according to claim 1 wherein said layer of padding material is affixed to said splinting material by diffusion of one of said layers into the surface of said other layer by heating at least one of said layers.

18. A splint according to claim 1 wherein said layer of padding material has a thickness of at least about 1/32 of an inch.

19. A splint according to claim 1 wherein said layer of padding material has a thickness of at least about 1/16 th of an inch to about three inches.

20. A splint according to claim 1 wherein said sheet of splinting material has a thickness of at least about 1/32 nd of an inch.

21. A splint according to claim 1 wherein said sheet of splinting material has a thickness of at least about 1/16 th of an inch to about ½ of an inch.

22. A splint according to claim 1, further comprising a layer of covering disposed over said padding material and substantially coterminous therewith.

23. A splint according to claim 22 wherein said layer of covering is a woven fabric.

24. A splint according to claim 22 wherein said layer of covering is a non-woven fabric.

25. A splint according to claim 22 wherein said layer of covering is a closed cell foam.

26. A splint according to claim 22 wherein said layer of covering is a polymeric film.

27. A splint according to claim 22 wherein said layer of covering is a non-woven fabric laminated to a reticular foam.

28. A splint according to claim 22 wherein said layer of covering is a non-woven fabric laminated to a polymeric film.

29. A splint of claim 1, wherein said gelatinous viscoelastic material comprising predominantly a member selected from the group consisting of a polyurethane, a polyvinyl chloride, and a silicone.

30. A splint according to claim 1, wherein said splinting material comprises poly(epsilon-caprolactone).

31. A splint according to claim 1, wherein said splinting material melts or softens at a temperature in the range of from 100° to about 175° F.

32. A splint of claim 3, wherein said padding consists essentially of said polyurethane.

33. A splint according to claim 7, wherein said padding material has a thickness and compressibility such that a per square inch compression force of between about one to about three pounds will reduce said thickness of said padding about 75% of its unloaded thickness over the area of compression.

34. A splint for being directly formed on a body part comprising:
    a. A sheet of low temperature thermoplastic splinting material;
    b. A layer of compressible gelatinous viscoelastic padding material comprising predominantly a member of the group consisting of a polyurethane, a polyvinyl chloride, and a silicone.

35. A splint according to claim 34, wherein said layer comprises predominantly said silicone.

36. A splint according to claim 1 wherein said layer of padding material is affixed to said splinting material by an intermediate layer of pressure sensitive adhesive coating.

* * * * *